(12) United States Patent
Chelle

(10) Patent No.: US 11,045,483 B2
(45) Date of Patent: Jun. 29, 2021

(54) PAIN-KILLING COMPOSITION COMPRISING A SALICYLIC ACID DERIVATIVE

(71) Applicant: AB7 INNOVATION S.A.S.U, Deyme (FR)

(72) Inventor: Rene Chelle, Deyme (FR)

(73) Assignee: AB7 INNOVATION S.A.S.U., Deyme (FR)

(*) Notice: Subject to any disclaimer, the term of this patent is extended or adjusted under 35 U.S.C. 154(b) by 459 days.

(21) Appl. No.: 15/749,348

(22) PCT Filed: Aug. 9, 2016

(86) PCT No.: PCT/FR2016/000129
§ 371 (c)(1),
(2) Date: Jan. 31, 2018

(87) PCT Pub. No.: WO2017/025666
PCT Pub. Date: Feb. 16, 2017

(65) Prior Publication Data
US 2018/0221392 A1 Aug. 9, 2018

(30) Foreign Application Priority Data
Aug. 12, 2015 (FR) .................. FR1501724

(51) Int. Cl.
| | | |
|---|---|---|
| *A61K 31/618* | (2006.01) | |
| *A61K 36/45* | (2006.01) | |
| *A61K 36/53* | (2006.01) | |
| *A61K 47/32* | (2006.01) | |
| *A61K 47/34* | (2017.01) | |
| *A61K 9/00* | (2006.01) | |
| *A61K 31/352* | (2006.01) | |
| *A01K 13/00* | (2006.01) | |
| *A61K 36/534* | (2006.01) | |
| *A61K 36/899* | (2006.01) | |
| *A61K 36/23* | (2006.01) | |
| *A61P 19/02* | (2006.01) | |
| *A61P 29/00* | (2006.01) | |
| *A61K 31/35* | (2006.01) | |

(52) U.S. Cl.
CPC .......... *A61K 31/618* (2013.01); *A01K 13/003* (2013.01); *A61K 9/0017* (2013.01); *A61K 31/35* (2013.01); *A61K 31/352* (2013.01); *A61K 36/23* (2013.01); *A61K 36/45* (2013.01); *A61K 36/53* (2013.01); *A61K 36/534* (2013.01); *A61K 36/899* (2013.01); *A61K 47/32* (2013.01); *A61K 47/34* (2013.01); *A61P 19/02* (2018.01); *A61P 29/00* (2018.01)

(58) Field of Classification Search
CPC ...... A61K 36/45; A61K 36/53; A61K 36/534; A61K 2300/00; A61K 31/352; A61K 31/618; A61K 36/23; A61K 36/899; A61K 31/35; A61K 47/32; A61K 47/34; A61K 9/0017; A01K 13/003; A61P 19/02; A61P 29/00
USPC ......................................... 424/732, 747, 745
See application file for complete search history.

(56) References Cited

U.S. PATENT DOCUMENTS

| | | | |
|---|---|---|---|
| 8,802,736 B2 | 8/2014 | Bucks et al. | |
| 8,865,234 B1 | 10/2014 | Reddy et al. | |
| 2005/0100588 A1* | 5/2005 | Kartheus ................. | A61L 15/44 424/449 |

FOREIGN PATENT DOCUMENTS

| | | | | |
|---|---|---|---|---|
| AU | 3723589 A | 1/1990 | | |
| CA | 2383806 A1 | 10/2002 | | |
| CN | 101757117 A | 6/2010 | | |
| CN | 104491767 A | 4/2015 | | |
| DE | 102010052939 A1 | 5/2012 | | |
| EP | 2047845 A1 * | 4/2009 | ........... | A61K 9/7076 |
| EP | 2047845 A1 | 4/2009 | | |
| FR | 2901132 A1 | 11/2007 | | |
| FR | 2901172 A1 | 11/2007 | | |

OTHER PUBLICATIONS

Uniquely Emu Products, Inc.: PRO80 For Sore Muscles & Joints 2 oz, retrieved from the internet: http://www.uniquelyemu.com/UE2002/PRO80-For-Sore-Muscles--Joints-2-oz.htm [retrieved on Jan. 18, 2018].

Wintergreen DL Brochure, retrieved from the internet: http://wintergreen.co.za/wp-content/uploads/2014/09/Wintergreen-DL-Brochure_Web-download.pdf [retrieved on Jan. 18, 2018].

Nawaz et al. "Clinical efficacy of polyherbal formulation Eezpain spray for muscular pain relief", Pakistan Journal of Pharmaceutical Sciences, Faculty of Pharmacy, University of Karachi, Pakistan. Jan. 1, 2015; vol. 28, pp. 43-47.

(Continued)

*Primary Examiner* — Aaron J Kosar
(74) *Attorney, Agent, or Firm* — Benoit & Cote, Inc.; Philip L. Conrad

(57) ABSTRACT

The subject-matter of the present invention is the use of a therapeutic composition comprising, in an applying carrier, at least one essential oil for relieving muscle and/or joint pain in an animal subject, wherein said composition topically treats an area of the skin of said subject, characterized in that said composition comprises methyl salicylate, which constitutes, with at least one essential oil of the composition containing same in only a small amount or not at all, an active agent within which the rate of transport of the methyl salicylate through the skin is increased by virtue of the oil, which is an essential oil.

9 Claims, 2 Drawing Sheets

(56) References Cited

OTHER PUBLICATIONS

Mehta et al. "Development and evaluation of antiarthritic herbal ointment", Research Journal of Pharmaceutical, Biological and Chemical Science. 2013; vol. 4, pp. 221-228.
Higashi et al. "Efficacy and Safety Profile of a Topical Methyl Salicylate and Menthol Patch in Adult Patients With Mild to Moderate Muscle Strain: A Randomized, Double-Blind, Parallel-Group,Placebo-Controlled, Multicenter Study", Clinical Therapeutics. 2010; vol. 32, pp. 34-43.
Herman et al. "Essential oils and their constituents as skin penetration enhancer for transdermal drug delivery: a review" Journal of Pharmacy and Pharmacology. 2014; vol. 67, pp. 473-485.
Bharti et al."Percutaneous Permeation Enhancement by Terpenes: Mechanistic View", The AAPS Journal. 2008; vol. 10, pp. 120-132.
Aqil et al."Status of terpenes as skin penetration enhancers", Drug Discovery Today, Elsevier. 2007; vol. 12, pp. 1061-1067.
Morra et al. "Serum Concentrations of Salicylic Acid Following Topically Applied Salicyclate Derivatives", Pharmacokinetics. 1996; vol. 30, pp. 935-940.
Cross et al. "Topical penetration of commercial salicyclate esters and salts using human isolated skin and clinical microdialysis studies", British Journal of Clinical Pharmacology. 1998; vol. 46, pp. 29-35.
Charoo et al. "Transdermal Delivery of Flurbiprofen: Permeation Enhancement, Design, Pharmacokinetic, and Pharmacodynamic Studies in Albino Rats", Pharmaceutical Development and Technology. 2005; vol. 10, pp. 343-351.
Jacobi et al. "Porcine ear skin: an in vitro model for human skin", Skin Research and Technology. 2007; vol. 13, pp. 19-24.
International Search Report of PCT/FR2016/000129; Rijswijk; Nov. 29, 2016; Gradassi, Giulia.

\* cited by examiner

PAIN-KILLING COMPOSITION COMPRISING A SALICYLIC ACID DERIVATIVE

The present invention lies within the field of use of a composition comprising an active agent intended to induce a systemic action in a target.

More precisely, the present invention relates to a use of a composition containing an active agent consisting of at least one salicylic acid derivative intended for a topical application to relieve muscle and/or joint pain in a subject.

As with all living beings, the phenomenon of aging of the tissues is coupled with a reduction in muscle tone. This reduction can sometimes be accompanied by other discomfort such as pain and tingling felt in different parts of the body, particularly the muscles, joints and tendons.

Arthritis is a joint disease resulting in degeneration of the cartilage. The cartilage, as it dehydrates, loses its elasticity and flexibility, becomes thinner and can sometimes disappear. Arthritis manifests itself as pain that is accentuated by the cold. It also results in stiffness of the limbs and thus reduces the motor skills of the subject affected. The situation is even more uncomfortable when muscle problems combine with arthritis, further penalizing the affected subjects as regards their mobility and motor skills for performing simple everyday gestures.

Numerous active ingredients exist, both of natural origin and as a result of synthesis, used to overcome this discomfort when the subject experiences sensations of muscle and joint pain ranging from slight to acute. In this field, salicylic acid and its derivatives are the anti-inflammatory active ingredients commonly used and also known for their efficacy.

For centuries, the use of essential oils has been known due to their numerous properties, namely antalgic, anti-inflammatory, draining, relaxing, stress-relieving, anti-bacterial and antifungal. For ease of use, essential oils are often formulated either in semi-solid form (ointments, creams, gels) or in liquid form (milks, emulsions, lotions). Moreover, permeation agents are systematically added to these formulations. In fact, they are intended for a topical application which, in order to produce the desired systemic effects, requires repeated and inconvenient applications throughout the day (Morra P. et al., 1996; 30: 935-940).

Several factors influence absorption through the skin, namely the formulation of the active substance, its method of application onto the skin, which takes into account the area of skin exposed, the dose per unit of area, the contact time and multiple applications. It has long been established that a substance, instead of passing entirely through the skin, can remain partly on the skin and can constitute a reservoir and be later released, or not. This effect is observed particularly with methyl salicylate when the latter is used in a topical application. In fact, in the event of a topical application of these formulations, not only does a large proportion of the methyl salicylate remain on the surface of the skin but also a time of around 60 minutes must elapse before it can be detected in the circulatory system (Sheree E. Cross et al., 1998; 46: 29-35) before inducing a systemic action.

In topical application carriers, the essential oils are dispersed in at least one vegetable oil, which plays a dual role, namely the role of dispersant and that of emollient in order to encourage the transdermal passage of the active molecules of the essential oils.

In the human and animal field, for systemic treatments by means of a solid topical application carrier releasing the active agent, the prior art discloses at least two types of systems. On the one hand, reservoir-based systems formed by at least one membrane permeable to said active agent and one reservoir in which is stored said agent formulated either as a liquid or a gel. On the other hand, multi-layer matrix systems of which at least one layer, the one in contact with the skin, is adhesive.

Admittedly, this avoids repeated applications but does not necessarily eliminate certain drawbacks such as the irritations and allergies caused by certain hydrophilic solvents such as alcohols, not to mention clogging of the pores connected with the prolonged wearing of these devices.

Specific permeation promoting agents are frequently associated with the two above-mentioned systems in order to promote the transdermal passage of the active agent through the skin, more precisely to pass through the stratum corneum and thus induce a systemic action. Such permeation agents are conventionally known to a person skilled in the art, namely specifically fatty acids, fatty acid esters comprising 10 to 20 atoms of carbon, fatty acid lactate esters, monoglycerides and their derivatives, acyl lactates and lower alcohols comprising 2 to 4 carbon atoms The French patent FR2901172 describes a method for incorporating a liquid, specifically essential oils, in granules of polymers such as a copolymer of ethylene and vinyl acetate and a polyether block amide. But this patent in no way suggests using this technique to obtain a composition containing an active agent comprising at least one derivative of salicylic acid to relieve a subject's muscle and/or joint pain.

The French patent FR2901132 discloses a device for transdermal application loaded with active agents chosen from essential oils as well as synthetic molecules soluble in a vegetable oil. But this document in no way envisages a composition comprising an active agent consisting of at least one salicylic acid derivative and an essential oil for relieving joint and/or muscle pain in a subject.

It has been shown that if methyl salicylate is used as the active ingredient in a composition, a large proportion of this compound fails to pass through the epidermis if a cream, gel or liquid formulation containing it is applied topically (Sheree E. Cross et al., 1998, 46: 29-35). This phenomenon is explained specifically by the low rate of hydrolysis of the salicylic acid derivative by the esterases of the skin. The transdermal passage speed of the methyl salicylate is therefore reduced. It is known that the stratum corneum or corneous layer forms a watertight barrier so that many molecules cannot pass through it in order to reach the circulatory system. Consequently, the use of permeation agents is one of the reliable approaches that facilitates transepidermal passage; but in a general way, these agents interact with some of the components of the stratum corneum in order to increase the penetration of the active molecules so as to induce a systemic action (Charoo Nasseem et al., 2005, 10: 343-351) which constitutes a drawback.

Since the salicylic acid derivative has a low transcutaneous passage speed, the topical compositions containing it must be applied several times. This therefore causes a problem of accumulation of the salicylic acid derivative, particularly salicylate salts on the surface of the skin (Neubert R. et al., 1990; 176: 711-716).

The Canadian patent No. 2383806 discloses a composition containing methyl salicylate, coconut oil and an essential oil to treat pain by topical application. In the composition, methyl salicylate is regarded either as a dilating agent or as an active ingredient and is mixed with a cetyl alcohol. The essential oils of rosemary, camphor, birch, laurel and sage can be present in the composition. The Australian patent No. 3723589 describes an anti-inflammatory composition comprising a copper salicylate salt, methyl salicylate and other essential oils such as eucalyptus, mint and rosemary. The U.S. Pat. No. 8,802,736 discloses an anti-inflammatory composition comprising a TRPV1 selective antagonist (capsaicin and its derivatives) and methyl salicylate as a solvent capable of solubilizing said antagonist. The aim of this patent is to increase the permeation speed of the capsaicin. Document DE102010053939 describes a composition for the treatment of muscle pain comprising heparin, menthol, hydroxyethyl salicylate, Diclofenac and rosemary essential oil, the function of which is to stimulate blood circulation. The European patent EP2047845 describes an anti-inflammatory adhesive preparation comprising methyl salicylate and 1-menthol, where the latter serves to limit the evaporation of the methyl salicylate, and an agent to promote the percutaneous absorption of methyl salicylate, which must be present in strong concentration in the preparation. The document published on Dec. 31, 2014, entitled "*Essential oils and their constituents as skin penetration enhancer for transdermal drug delivery: a review*" written by Anna Herman et al., describes mechanisms of action involving essential oils and their major constituents as skin permeation agents for the transdermal administration of drugs. Methyl salicylate is absent from the list of active ingredients. The document published on Feb. 8, 2008, entitled "*Percutaneous permeation enhancement by terpenes: mechanistic view*," written by Bharti Sapra et al., describes mechanisms whereby terpenes increase the transdermal permeation of drugs, i.e., the interaction of drugs with the lipid layer of the stratum corneum (SC) or the increase of their solubility vis-à-vis of the lipids of the SC. 1,8-cineole improves the transcutaneous passage of 5-fluororacil, Zidovudine, mefenamic acid; menthol, that of Nicardipine hydrochloride, Zidovudine; linalool, that of Haloperidol and Zidovudine. Methyl salicylate is absent from the list of active ingredients. The document published on Oct. 17, 2007, entitled "*Status of terpenes as skin penetration enhancers*," written by Aqil Mohammed et al., describes applications of terpenes as promoters of drug permeation through the skin. Menthol and geraniol are referred to therein as permeation agents of hydrophilic drugs such as caffeine, imipramine hydrochloride; linalool and 1,8-cineole for propranolol hydrochloride. Methyl salicylate is absent from the list of active ingredients. But none of the documents of the prior art disclose the use of a composition comprising methyl salicylate whose the rate of transcutaneous transport is increased.

Therefore, there is a need to provide a new use of a composition containing an active agent comprising a salicylic acid derivative, namely methyl salicylate whose skin rate penetration is faster, said active agent being capable of causing a systemic action to relieve muscle and/or joint pain, even tendinitis, in an animal subject. There is also a need to increase the therapeutic action of pain relief by increasing the rate of transport of methyl salicylate through the skin.

The present invention proposes to overcome the abovementioned drawbacks by providing a use of a composition comprising an active agent consisting of at least one salicylic acid derivative and at least one auxiliary essential oil in a topical application carrier in order to induce a systemic action in a subject to relieve muscle and/or joint pain.

Figure 1:
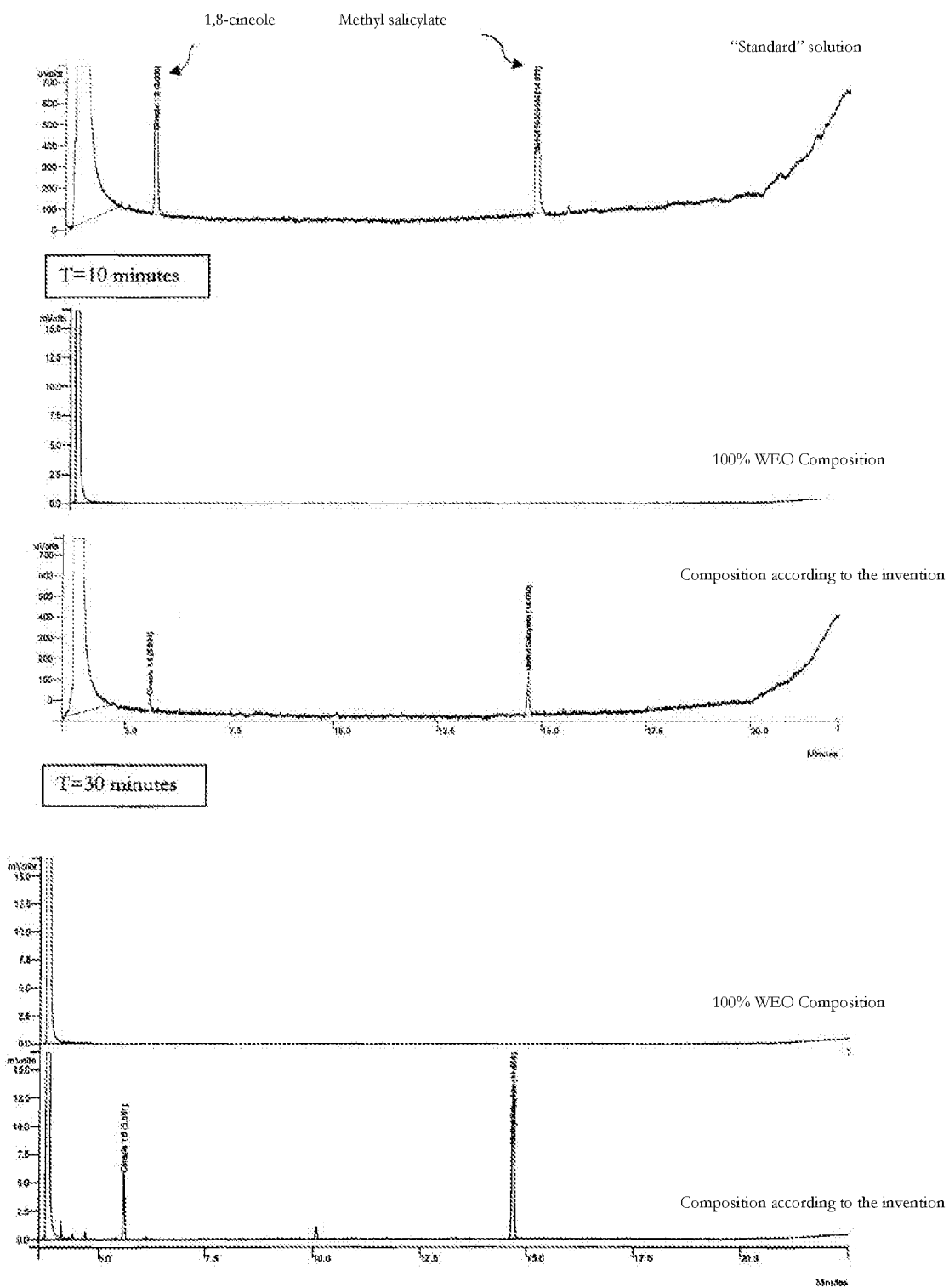
FIG. 1 shows chromatograms from a composition comprising the active agent, according to the invention, deposited on the skin surface of a pig's ear.

Thus, a first subject matter of the present invention is an use of a therapeutic composition containing, in an application carrier, at least one essential oil to induce relieving muscle and/or joint pain in an animal subject, said composition topically treating an area of skin of said subject, characterized in that said composition comprises methyl salicylate which constitutes, with at least one essential oil of the composition containing same in only a small amount or not at all, an active agent within which the rate of transport of the methyl salicylate through the skin is increased by virtue of the essential oil.

According to the use of the invention, the composition contains an active agent comprising methyl salicylate and at least one auxiliary essential oil, said active agent being contained in a topical application carrier, to relieve muscle and/or joint pain and thus improve the vitality of an animal subject. The methyl salicylate is advantageously brought in the composition by wintergreen essential oil; its total quantity in the composition is such that it provides relief from muscle and/or joint pain in an animal subject by a systemic action.

Advantageously, wintergreen essential oil constitutes between 1 and 15% by weight and the auxiliary essential oil(s) used constitute(s) from 0.15 to 9% by weight in relation to the total weight of the assembly consisting of all of the essential oils of the composition incorporated in its topical application carrier for implementation in the use. Preferably, methyl salicylate constitutes from 52 to 85% by weight of the total weight of the active agent. The auxiliary essential oil can constitute between 15 and 48% by weight of the total weight of the active agent. In these conditions, pain relief can occur without the accumulation of methyl salicylate in the area of skin to be treated.

In the context of the present invention, "vitality" means the physical condition of the subject which translates into relief from muscle and/or joint pain and a regain of muscle tone due to venous and lymphatic decongestion.

"Animal subject" means the target, whether human or animal, specifically a pet such as a dog, cat or horse.

"Auxiliary essential oil" means an essential oil or a mixture of essential oils extracted from a plant whose function is to cause the methyl salicylate to pass through the skin, said essential oil containing only a small amount of methyl salicylate, meaning that only a small quantity of the latter, less than 1%, can be found therein.

Unexpectedly, the inventor observed that when an active agent consists of a salicylic acid derivative, specifically methyl salicylate, associated with at least one essential oil, the methyl salicylate can be induced by a so-called "auxiliary" essential oil so that the assembly passes through the cutaneous barrier in the area of skin to be treated. The auxiliary essential oil increases the rate of transdermal penetration and transport through the skin of a salicylic acid derivative. In this way, on the one hand, the salicylic acid derivative, in this case methyl salicylate, no longer accumulates on the surface of the area of skin to be treated and, on the other hand, it is no longer necessary to perform repeated topical applications of a composition containing said active agent in order to achieve a joint and/or muscle pain relieving effect in the subject treated.

According to the use of the composition of the invention, the salicylic acid derivative is methyl salicylate. Methyl salicylate can be introduced into the composition by wintergreen essential oil (*Gaultheria procumbens* and *Gaultheria fragrantissima*), which can contain up to 100% by weight thereof.

According to the use of the composition of the invention, it uses at least one auxiliary essential oil advantageously containing at least one monoterpene alcohol. The monoterpene alcohols are preferably taken from the group formed by 1,8-cineole, menthol, geraniol, linalool or a mixture thereof; said alcohols have the property of being capable of passing spontaneously through the skin barrier. Furthermore, auxiliary essential oil, in addition to its above mentioned property, also has beneficial effects for the subject treated, such as muscle relaxation, muscle tension reduction or even vasodilation.

According to the use of the composition of the invention, it uses auxiliary essential oil that is advantageously officinal rosemary essential oil (*Rosmarinus officinalis*), which contains 1,8-cineole.

According to the use of the composition of the invention, as essential oil, it uses auxiliary essential oil comprising essential peppermint oil (*Mentha pperita*), which contains menthol and/or Ceylan essential oil (*Cymbopogon nardus*), which contains geraniol and/or coriander essential oil (*Coriandrum sativum*), which contains linalool.

The total quantity of monoterpene alcohols in the composition must not cause an allergic or toxic reaction in the subject treated.

The composition also comprises a topical application carrier.

According to the use of the composition of the invention, said topical application carrier is a fluid taken from the group formed by a liquid whose viscosity enables distribution by aerosol, a shampoo, a lotion, a milk or an emulsion.

According to another use of the composition of the invention, the topical application carrier can take the form of a gel, ointment or cream.

According to the use of the composition of the invention, the topical application carrier is a polymer matrix in which the active agent is incorporated.

In a first alternative, said polymer matrix is formed from a copolymer of ethylene and vinyl acetate (EVA), whose vinyl acetate content is between 15 and 60% by weight.

In a second alternative of the use of the composition of the invention, the polymer matrix is a thermoplastic polymer chosen from the group formed by the ester- or ether-based thermoplastic polyurethane elastomers, absorbent-grade copolyamides and polyamides (PA), such as PA6, PA10, PA12, absorbent-grade polyether block amides, absorbent-grade polyethylenes, starch-grafted polyethylenes, polyesters, styrene polymers such as SEBS, SIS, polyolefins, vinyl polychlorides or a mixture thereof, the active agent being incorporated in said matrix.

In a third alternative of the use of the composition of the invention, the polymer matrix is an isocyanate- and polyol-based cross-linked polyurethane or an isocyanate- and polyamine-based polyuria. The cross-linked polyurethane is obtained from a polyol resin that is liquid or made liquid and an isocyanate that is liquid or made liquid and one then shaped by casting. The cross-linked polyuria is obtained from a polyamine resin that is liquid or made liquid and an isocyanate that is liquid or made liquid and one then shaped by casting. The isocyanate is chosen from the group formed by isocyanates with at least 2 functions, having an aromatic or aliphatic structure. Examples include TDI (toluene diisocyanate), HDI (hexamethylene diisocyanate), MDI (diphenylmethylene diisocyanate), H12MDI (dicyclohexylmethane diisocyanate), IPDI (isophorone diisocyanate), NDI (naphthalene diisocyanate), TODI (O-tolidine diisocyanate), PPDI (para-phenylene diisocyanate) and their prepolymers.

The polyol resin is chosen from that having at least 2 hydroxyl functions, with a long or short chain, based on polyesters, polyethers, polythioethers, polyacetals, polycarbonates, polyesteramides, naturally hydroxylated or modified vegetable oils or a mixture thereof. The polyamines are those having at least 2 amine functions, chosen from polyetheramines, aliphatic or aromatic.

The incorporation method of at least one liquid active agent in the above mentioned cross-linked polyurethane polymer is performed according to the teachings of the French patent FR2992325. The method involves mixing, at ambient temperature, the liquid composition with the liquid polyol phase until a homogenous mixture is obtained. At the same time, the liquid isocyanate phase is prepared. Next, the two phases are mixed by agitation for about 30 seconds, then the homogenous liquid mixture obtained is poured into a mold to form the matrix.

If the topical application carrier is a polymer matrix, the latter takes the form of a "monoblock" device, meaning that it has neither a regulation membrane controlling the evaporation of the incorporated salicylic acid derivative nor an adhesive layer to encourage contact with the skin. Said polymer matrix can be shaped into devices such as collars, bracelets, patches and suchlike that are held against the skin by means, for example, of an orthosis.

In the case of a thermoplastic polymer matrix topical application carrier, said matrix is shaped by plastics processing techniques well known to a person skilled in the art, namely by extrusion, injection molding or pressing. The incorporation method of the composition in the polymer can be achieved according to the teachings of the French patent FR2901172. This method allows a liquid containing one or more active substances to be incorporated cold into a polymer, at a temperature ranging from 1 to 5° C. above its vitreous transition temperature.

When the topical application carrier is a polymer matrix, the latter represents between 80 and 90% by weight in relation to the total weight of the composition. If the matrix is an EVA copolymer, it is preferably formed from EVA copolymer granules or powder whose vinyl acetate content is between 15% and 60% by weight.

According to the use of the composition of the invention, the composition contains at least one formulation additive chosen on the basis of the topical application carrier used. The formulation additives can be a vector promoting the release of the active agent from the topical application carrier or agents participating in the structure and/or shaping of said carrier. The formulation additives can be chosen from water, vegetable oils, water-miscible solvents, inert fillers of mineral origin in the form of powder, gelling agents, colorants, surfactants, propellant gas, thickening agents, synthetic or natural perfume or a mixture thereof.

The assembly of formulation additives and the application carrier can represent up to 98% by weight of the total weight of the composition implemented in the use.

The actual quantities of each of the constituents of the active agent are calculated so that, on the one hand, the accumulation of methyl salicylate in the area of skin to be treated is avoided and, on the other, a relatively fast systemic action is induced.

The vegetable oil is chosen from oil from refined copra, refined macadamia, evening primrose, lemon, sweet almond, tamanu or a mixture thereof. Vegetable oil improves the miscibility of the wintergreen essential oil and the auxiliary essential oil together. It also dilutes the concentration of the mixture of essential oils within the liquid composition. Incidentally, vegetable oil plays the role of dispersant of the essential oils. If vegetable oil is present, its quantity varies between 5 and 15% by weight in relation to the total weight of the active agent.

The mineral fillers are chosen from the group formed by talc, zinc or titanium oxides, micas, silica, calcium carbonate, clay particles, cork or a mixture thereof. If the application carrier is a polymer matrix, the purpose of said fillers is to improve the mechanical strength of the composition and also to boost the release of the active agent. In fact, if the total quantity of said fillers in the composition is large, the active agent release speed is accelerated. If the fillers are present in the composition, they are preferably mixed directly with the polymer in a quantity varying between 0.1 and 5% by weight of the composition.

The colorants are those commonly used and known to a person skilled in the art. They can be in solid form as granules or powder, or in liquid form. If colorant is present, it is mixed directly with the topical application carrier used.

The perfume can be natural or synthetic and its quantity can represent between 0 and 15% by weight of the composition implemented in the use. It can be introduced directly by one of the essential oils of the composition. The perfume is, for example, chosen from the perfume of vanilla, lime, lavender, violet, apple, apricot, patchouli or green bamboo leaves and can be adapted as desired by the end user.

The thickening agents are those commonly used in cosmetic creams. They are chosen from the group formed by gum arabics, saturated fatty acids, linear or branched, such as palmitic acid, stearic acid, myristic acid, lauric acid and their mixtures, saturated fatty alcohols, linear or branched, such as cetyl alcohol and stearyl alcohol.

If the topical application carrier is a liquid, a cream, a gel or an ointment, the surfactants are those usually used in cosmetic formulations in the form of lotion, milk, shampoo, emulsion, cream, gel or ointment. They are anionic, cationic or zwitterionic surfactants depending on the topical application carrier chosen. They are chosen from the group formed by glycol esters, polyoxyethyleneglycol esters, sorbitan esters, fatty alcohol ethers, lipo-amino-acids, sulfonamides, quaternary ammoniums and betaines.

The gelling agents are those currently used in the cosmetic formulations of gel. They are chosen from the group formed by hydroxyethylcellulose, hydroxypropylcellulose, methylcellulose, carboxymethyl cellulose, agar, pectins, algins, carrageenans, gelatin or even polysaccharides and carboxyvinyl polymers.

The water-miscible or at least partly water-miscible solvents are polyols such as glycerine, glycols or polyethylene glycols or mixtures thereof.

The propellant gases are chosen from propane, butane, isobutene or even dimethyl ether.

The various constituents of said composition are mixed together by simple agitation, for example in a mixer, at ambient temperature, until homogenization.

Yet other subject matter of the present invention consists in the use of a composition having the abovementioned characteristics in order to induce topical relieving muscle and/or joint pain in an animal subject in the area of skin to be treated, particularly in order to relieve arthritic pain.

According to the use of the composition according to the invention, if the topical application carrier is a polymer matrix and if the subject to be treated is an animal, said composition matrix is held by a bond against the skin of the animal subject to be treated for a sufficient time to enable relief to be felt. The device is effective for a long period ranging from several days to eight weeks and can be worn continuously.

To confirm that a salicylic acid derivative, specifically methyl salicylate, is trained by the auxiliary essential oil in order to pass through the skin, a permeation test was performed. In that case, it is referred to the protocols described in the European Pharmacopeia (01/2008:1011) and in literature (Jacobi U. et al.,*Skin research and technology.* 2007, 3) for transdermal diffusion devices. The working temperature is set at 32° C.

The use according to the invention implements the composition deposited on the outer surface of a membrane, itself in contact by its inner face with the receiving medium. It was decided to use the skin of a pig's ear as the membrane and a Water/Ethanol (50/50) mixture as the receiving medium. The receiving medium must be in contact with the skin and no air bubbles must be present.

The receiving medium is then removed after a precise time for analysis by gas chromatography. The mixtures obtained are compared to a control solution containing 1,8-cineole as a marker of rosemary essential oil and methyl salicylate as a marker of wintergreen essential oil.

The following examples are used by way of indication to illustrate the invention without limiting its scope.

EXAMPLE

The use of a composition comprising an active agent consisting of essential oils of wintergreen and of officinal rosemary to relieve joint pain in a dog.

The following products are available:

A wintergreen essential oil marketed by NATURARUM. This essential oil contains between 98 and 100% by weight of methyl salicylate;

A official rosemary essential oil marketed by INTERAXION. This essential oil contains between 50 and 55% by weight of 1,8-cineole;

A refined copra oil marketed by INTERAXION;

Granules of copolymers of ethylene and vinyl acetate (EVA) marketed by GAZECHIM under the brand EVA ALCUIDA PA-538 which contains 18% by weight of vinyl acetate. The vitreous transition temperature of this polymer is given as 68° C.;

A chocolate brown colorant in the form of granules sold by ELIAN under the brand P4625C.

The following equipments are available:

a PAPPENMEIER cylindrical reactor with a capacity of 8 liters provided with an agitator driven by a variable speed motor;

a SANDRETTO injection press, Series 8, generating a pressing capacity of 150 tonnes;

a mold made of steel mounted on said press whose four fingerprint are in the form of a collar having 75 cm long.

The temperature diagram of the sheath, from the hopper to the nozzle, is as follows: 115° C. (Zone 1), 125° C. (Zone 2), 130° C. (Zone 3), 135° C. (Zone 4) with a holding time of 3 seconds at 65 bars and a mold temperature of 155° C.

a VARIAN® gas chromatograph, provided with a 20000 Da polyethylene glycol column, Optima-Wax 0.25-30 m×0.32 mm ID.

Procedure a—Preparation of the active agent of the composition:

It is introduced consecutively in a beaker of 250 mL, at ambient temperature, 74 g of wintergreen essential oil and 26 g of rosemary essential oil. 12 g of refined copra oil are added in order to better disperse the two essential oils. Low agitation is performed using a bar magnet in order to obtain a homogenous mixture to obtain the liquid composition.

135 mg of the composition obtained above is weighed and applied directly onto the skin of a pig's ear over an area of 7.1 cm², according to the procedure previously described. The volume of the Water/Ethanol (50/50) receiving medium is 140 mL. Samples of the receiving medium are taken after 10 minutes and 30 minutes. The chromatogram obtained is shown in FIG. 1.

FIG. 1: Chromatogram of the composition comprising the active agent according to the invention, deposited on the skin surface of a pig's ear.

It will be observed that in the presence of officinal rosemary essential oil (REO), the passage speed of the wintergreen essential oil (WEO) is increased. This result confirms that the transcutaneous passage of methyl salicylate is trained by the officinal rosemary essential oil. By contrast, if the composition contains an active agent consisting solely of wintergreen essential oil, the methyl salicylate fails to pass through the skin even after 30 minutes.

b—Incorporation of the composition in EVA:

The reactor is preheated to 70° C. in an oil bath. 830 g of EVA granules are introduced, under slight agitation, until the temperature measured within said granules is around 70° C. Still under slow agitation, introduce the liquid composition previously obtained into the reactor. This is agitated until all of the liquid is completely absorbed by the polymer, then the temperature is reduced to 25° C. On completing incorporation, the EVA granules are dry and slightly swollen. Finally, 20 g of brown colorant, still under slow agitation, are introduced. The reactor is emptied and the compound thus obtained is stored in a pack hermetically sealed against air and humidity. The EVA granules obtained upon completing this step contain 10% by weight of wintergreen essential oil (WEO) and 3.5% by weight of officinal rosemary essential oil (REO).

c—Shaping the compound into a collar

The compound obtained at step b) of the procedure is injected into collars weighing around 41 g at the outlet of the nozzle for a length of 75 cm.

Assessment of the Rate of Transdermal Passage of Methyl Salicylate

To perform this assessment, the mass of the collar is determined so as to satisfy the conditions of "sink" handling, i.e., that the maximum rate of active ingredient released into the medium must be less than 10% of the saturating concentration of the active ingredient in this medium. The receiving medium is taken, then analyzed by chromatography.

1 g of the collar obtained at step c) of the procedure, having a surface area of 3.1 cm², is weighed, in accordance with the above-described procedure. The experiment is performed for 72 hours, then 2 mL of the receiving medium are taken and analyzed by gas chromatography. The mixtures obtained are compared to a "standard" solution containing 1,8-cineole as a marker of the officinal rosemary essential oil and methyl salicylate as a marker of the wintergreen essential oil. The results are shown in FIG. 2.

Figure 2:
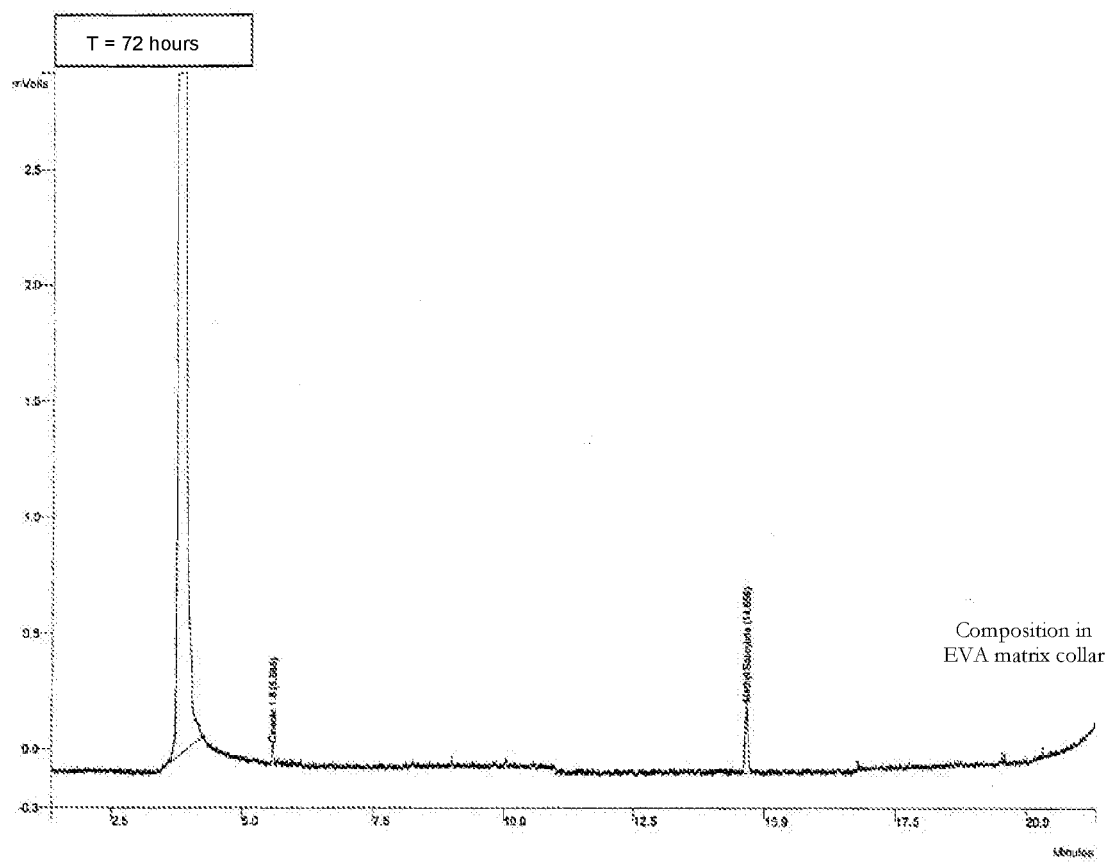
FIG. 2 is a chromatogram from a composition according to the invention where the topical application carrier is an EVA polymer matrix collar containing the composition.

FIG. 2: Chromatogram of the composition according to the invention of which the topical application carrier is an EVA polymer matrix collar containing the composition.

It will be observed that the methyl salicylate passed through the skin from the collar into the receiving medium because the two markers are detected therein. This shows on the one hand that the polymer matrix is capable of carrying the active agent so that the latter passes into the skin, and on the other hand that the officinal rosemary essential oil efficiently induces the passage of methyl salicylate through the skin of the pig's ear.

Table 1 below lists the rate transport of the methyl salicylate (MeSa) of the active agent according to the application carrier.

TABLE 1

Summary of the rate transport of methyl salicylate through the skin

| Test | Active Agent | Carrier | Rate (µg/mL/hour) |
|---|---|---|---|
| 1 | MeSa + rosemary essential oil | EVA collar | 0.232 |
| 2 | MeSa + rosemary essential oil | EVA collar | 0.102 |
| 3 | MeSa + rosemary essential oil | EVA collar | 0.269 |
| 4 | MeSa + rosemary essential oil | Copra oil | 327.4 |
| 5 | MeSa + citronella essential oil | Copra oil | 383.7 |
| 6 | MeSa + peppermint essential oil | Copra oil | 257.7 |

Efficacy Tests Performed on Dogs Suffering from Joint and Muscle Pain

The efficacy of the collar obtained in step c) of the procedure was assessed for a panel of four dogs selected from a kennel from those at least 8 years old showing clear signs of reduced mobility characterized specifically by difficulties in getting up and moving. Each of these four dogs wore, around its neck, a collar whose "composition/animal weight" ratio was previously determined by the size of the collar.

The animals were observed every day for six weeks without changing anything with respect to their food or their lifestyle.

After 48 hours, the most disabled of the four showed itself to be more alert and more reactive towards other dogs and the kennel owner and, moreover, had greater ease of movement.

After wearing the collar for four days, the four dogs showed significantly improved motor skills which translated into prolonged periods of standing and also spontaneous walks, particularly outside. The collar therefore improved the "vitality" of the dogs. This "vitality" effect was observed for six weeks in the most disabled dog.

The invention claimed is:

1. Therapeutic monoblock device comprising a polymer matrix topical application carrier and an active agent for inducing relieving muscle and/or joint pain in a human or animal subject, the monoblock device being free of an adhesive layer, said active agent comprising methyl salicylate provided by wintergreen essential oil, and an auxiliary essential oil, wherein the active agent is incorporated in the polymer matrix, wherein the polymer matrix is a copolymer of ethylene and vinyl acetate (EVA), whose vinyl acetate content is between 15 and 60% by weight, and the polymer matrix represents 80 to 90% by weight of the device, and the active agent comprises 52 to 85% by weight of methyl salicylate, the rate of transport of the methyl salicylate through the skin being increased by virtue of the auxiliary essential oil.

2. Therapeutic monoblock device according to claim 1, wherein the auxiliary essential oil of the active agent constitutes between 15 and 48% by weight of the active agent.

3. Therapeutic monoblock device according to claim 1, wherein the auxiliary essential oil of the active agent is rosemary essential oil (*Rosmarinus officinalis*), peppermint essential oil, Ceylan citronella essential oil, coriander essential oil, or a combination thereof.

4. Therapeutic monoblock device according to claim 3, wherein the auxiliary essential oil contains at least one monoterpene alcohol chosen from the group formed by 1,8-cineole, menthol, geraniol and linalool.

5. Therapeutic monoblock device according to claim 1, wherein the essential wintergreen oil constitutes between 1 and 15% by weight of the total essential oil content of the device.

6. Therapeutic monoblock device according to claim 1, wherein the auxiliary essential oil constitutes from 0.15 to 9% by weight of the device.

7. Therapeutic monoblock device according to claim 1, wherein the active agent further comprises at least one formulation additive chosen from a vegetable oil, an inert filler of mineral origin, a dye, a surfactant, a synthetic perfume, a natural perfume, or a mixture thereof.

8. Therapeutic monoblock device according to claim 7, wherein said inert filler of mineral origin is a powder.

9. A method of topically inducing arthritic pain relief comprising applying the therapeutic monoblock device of claim 1 against the skin of a human or animal subject to be treated for a sufficient time to enable the pain relief.

* * * * *